United States Patent
Yang

(10) Patent No.: US 12,311,199 B2
(45) Date of Patent: May 27, 2025

(54) MONITOR FOR A RADIOTHERAPY DEVICE

(71) Applicant: ELEKTA BEIJING MEDICAL SYSTEMS CO., LTD, Beijing (CN)

(72) Inventor: Xiangjing Yang, Beijing (CN)

(73) Assignee: ELEKTA BEIJING MEDICAL SYSTEMS CO., LTD, Beijing (CN)

( * ) Notice: Subject to any disclaimer, the term of this patent is extended or adjusted under 35 U.S.C. 154(b) by 312 days.

(21) Appl. No.: 17/756,937

(22) PCT Filed: Nov. 26, 2020

(86) PCT No.: PCT/CN2020/131934
§ 371 (c)(1),
(2) Date: Jun. 6, 2022

(87) PCT Pub. No.: WO2021/109919
PCT Pub. Date: Jun. 10, 2021

(65) Prior Publication Data
US 2023/0001237 A1 Jan. 5, 2023

(30) Foreign Application Priority Data
Dec. 6, 2019 (CN) .......................... 201911243297.3

(51) Int. Cl.
*A61N 5/10* (2006.01)
(52) U.S. Cl.
CPC .......... *A61N 5/1048* (2013.01); *A61N 5/1081* (2013.01); *A61N 2005/1074* (2013.01)
(58) Field of Classification Search
CPC ...... A61N 5/10; A61N 5/1081; A61N 5/1048; G01M 1/32
See application file for complete search history.

(56) References Cited

U.S. PATENT DOCUMENTS

| 2006/0079763 A1 | 4/2006 | Jeung et al. |
| 2012/0168646 A1* | 7/2012 | Gutfleisch .............. G01M 1/32 250/492.1 |
| 2013/0272489 A1 | 10/2013 | Limoli et al. |

FOREIGN PATENT DOCUMENTS

| CN | 102805631 A | * 12/2012 |
| CN | 102933149 | 2/2013 |

(Continued)

OTHER PUBLICATIONS

"International Application Serial No. PCT/CN2020/131934, International Search Report dated Feb. 26, 2021", (Feb. 26, 2021), 4 pgs.

(Continued)

*Primary Examiner* — David E Smith
*Assistant Examiner* — Hsien C Tsai
(74) *Attorney, Agent, or Firm* — Schwegman Lundberg & Woessner, P.A.

(57) ABSTRACT

A monitor assembly for a radiotherapy device (220) is provided, the radiotherapy device (220) being configured to provide therapeutic radiation to a patient (208) via a source (200) of therapeutic radiation, and wherein the radiotherapy device (220) comprises a first rotatable member. The monitor assembly comprises a monitor (302) configured for outputting visual data to a user, a counterweight (406), and a connector assembly configured to connect the monitor (302) to the first rotatable member. A first part of the connector assembly is configured for rotation, with the first rotatable member, and a second part of the connector assembly is configured for non-rotation, with the monitor (302).

17 Claims, 5 Drawing Sheets

(56) References Cited

FOREIGN PATENT DOCUMENTS

| CN | 103796600 A | * | 5/2014 | ....... A61B 17/00234 |
|----|-------------|---|--------|------------------------|
| CN | 105916553 A |   | 8/2016 | |
| CN | 208943296 U |   | 6/2019 | |
| EP | 0919186 A2  |   | 6/1999 | |

OTHER PUBLICATIONS

"International Application Serial No. PCT/CN2020/131934, Written Opinion dated Feb. 26, 2021", (Feb. 26, 2021), 5 pgs.

"European Application Serial No. 20897531.8, European Search Report dated Dec. 8, 2023", (Dec. 8, 2023), 8 pgs.

* cited by examiner

MONITOR FOR A RADIOTHERAPY DEVICE

PRIORITY APPLICATIONS

This application is a U.S. National Stage Filing under 35 U.S.C. § 371 from International Application No. PCT/CN2020/131934, filed on Nov. 26, 2020, and published as WO2021/109919 on Jun. 10, 2021, which claims the benefit of priority to Chinese Application No. 201911243297.3, filed on Dec. 6, 2019; the benefit of priority of each of which is hereby claimed herein, and which applications and publication are hereby incorporated herein by reference in their entireties.

This disclosure relates to a monitor for a radiotherapy device.

BACKGROUND

Radiotherapy can be described as the use of ionising radiation to treat a human or animal body. In particular, radiotherapy is commonly used to treat tumours within the body and skin of a human or animal patient. In such treatments, the cells forming part of the tumour are irradiated by ionising radiation in order to destroy or damage them. However, in order to apply a prescribed dose of ionising radiation to a target location or target region, such as a tumour, the ionising radiation will typically also pass through healthy tissue of the human or animal body. Therefore, radiotherapy has the desirable consequence of irradiating and damaging a target region, but can also have the undesirable consequence of irradiating and damaging healthy tissue. It is desirable to minimise the dose received by healthy tissue in radiotherapy treatment. It is thus desirable to control the application of the radiotherapy treatment as effectively as possible.

Modern radiotherapy treatment uses techniques to target the tumour (or other target region) as accurately as possible and to reduce the radiation dose to healthy tissue, thereby providing a safer treatment for the patient. For example, a standard approach to minimising a radiation dose received by healthy tissue surrounding a target region is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment arc, in which the radiation source rotates through a certain angle. However, because the radiation is applied from a plurality of different angles, the same, high, cumulative radiation dose is not built up in any portion of the healthy tissue because the specific healthy tissue that the radiation passes through varies with angle. Therefore, each unit volume of the healthy tissue receives a smaller radiation dose, relative to a unit volume of the target region.

The effectiveness of any therapeutic radiotherapy treatment will be dependent on many contributing factors such as, but not limited to, the capabilities of the machine or device being used to apply the therapeutic radiation and the extent to which the user is able to control the operation of the device, in addition to unique factors pertaining to the individual patient and the nature of his or her tumour or other target region. The extent of user control can be dependent on the skill and experience level of the user and on the level of responsiveness of the radiotherapy device to the user's control signals. The user's control of the therapeutic radiotherapy device and his or her ability to monitor the patient's wellbeing also depends on the user being able to view and monitor the operation of the device, and the patient during the treatment, effectively.

The user of the therapeutic radiotherapy device needs to maintain good control over the various physical aspects of the device, whilst often also having to communicate with the patient and/or otherwise remain aware of the patient's needs and wellbeing. The user also needs to receive feedback about the operating parameters of the device, and should have visibility of the patient during treatment, to look after the patient's wellbeing and to ensure that the patient is not moving or doing anything else that could affect the application of the therapeutic radiotherapy.

In known therapeutic radiotherapy devices, such as known medical linear accelerator (LINAC) devices, a rotating gantry can have important operational devices mounted thereon, such as the source and/or the detector of the therapeutic radiation beam(s). It also may have imaging equipment mounted thereon. Known radiotherapy devices can also include other components such as the collimator, which is used for directional and shape control of the therapeutic radiation, generated within the device. The collimator forms part of a radiation source, which can be fixed to the gantry. In some arrangements, the collimator, or part of the collimator, can also be rotatable.

Known LINAC controllers can include one or more monitors, which comprise a screen or screens that output visual feedback to the user. This visual feedback can include visual images (still images and/or video) of the patient, often from more than one angle and/or at more than one level of magnification for a particular area. The monitors can also display information such as patient identity, the type, size and location of tumour and the prescribed treatment dosage or scheme. The monitors can also display information on current operating parameters for the device. For example, the information can include accessories information for the patient, treatment table position information, offset values, and so on.

It is desirable for the controls and monitoring of a therapeutic radiotherapy device to be as user-friendly as possible, in order to: increase the effectiveness of the radiotherapy for treating the target region; avoid damage to healthy tissue that could otherwise be caused by inaccurate targeting of the radiotherapy; increase the speed of radiotherapy and improve patient throughput; improve patient experience; improve the speed and facility with which a new or infrequent user of the device can understand, learn and retain how to use it; and limit the risk of user error or inaccuracy.

SUMMARY

An improved monitor and monitor assembly for a rotatable member, such as a gantry, of a therapeutic radiotherapy device is provided. The improved monitor and monitor assembly enable the user to monitor and thus to control operation of the radiotherapy device, such as a medical linear accelerator (LINAC) device, more easily, efficiently and accurately.

The monitor is configured to be provided substantially in the centre of a rotatable gantry, or at least to be surrounded by rotating aspects of the gantry such as the so-called gantry 'drum', but not itself to rotate with the rotating part(s) of the gantry. Instead, the monitor remains fixed—substantially in an upright position, so that the information displayed by the monitor can by readily viewed and understood at all times, by the user, regardless of the rotational position of other part(s) of the gantry.

The monitor may be connected to the gantry, or located within the gantry and connected to another part of the radiotherapy device, via any suitable connector or connector assembly. The connector or connector assembly may be configured so that one or more of its component parts rotates, or otherwise moves, with the gantry (or when the gantry rotates) and one or more of its other components remains stationary—or at least is configured to ensure that the monitor stays substantially stationary—when the gantry rotates. The connector or connector assembly may engage the monitor in any suitable manner. It may include a spring bias, to keep the monitor in place when other components move therearound. The connector or connector assembly may include means to ensure that the rotational centre of any rotationally-moving parts of the connector or connector assembly are aligned with a rotational centre of the gantry. The connector or connector assembly may be adjustable.

According to an aspect, a monitor assembly for a radiotherapy device is provided, said radiotherapy device being configured to provide therapeutic radiation to a patient via a source of therapeutic radiation, and wherein said radiotherapy device comprises a first rotatable member. The monitor assembly comprises a monitor configured for outputting visual data to a user, a counterweight, and a connector assembly configured to connect the monitor to the first rotatable member. A first part of the connector assembly is configured for rotation, with the first rotatable member, and a second part of the connector assembly is configured for non-rotation, with the monitor.

The first part of the connector may be configured for both rotational movement and substantially linear movement. It may be configured for simultaneous rotational and substantially linear movement and/or it may be configured for rotational movement and substantially linear movement at different respective times.

The counterweight may be configured for non-rotation, with the monitor. The counterweight may be integral to the connector assembly or it may be formed separately to the connector assembly. For example, the counterweight may be affixed to, connected to, or housed within, the connector assembly.

The connector assembly may comprise one or more component parts.

The first rotatable member may comprise a rotatable gantry. The rotatable gantry may have a radiation source (or radiation head) mounted thereon, or otherwise affixed thereto. It may also comprise a collimator, such as a block collimator or multi leaf collimator (MLC), for shaping and directing a beam of therapeutic radiation. The gantry may have imaging equipment mounted thereon.

The connector assembly may comprise a bearing assembly. The bearing assembly may include one or more bearings that are provided between the first part of the connector assembly, which is configured for rotation with the first rotatable member, and the second part of the connector assembly, which is configured for non-rotation with the monitor and the counterweight. The bearings may be configured to reduce friction or resistance between moving and non-moving components of the bearing assembly. The bearing assembly may comprise one or more grooves, indentations or receivers that are configured to receive a part of a rotatable member of a therapeutic radiotherapy device. For example, the bearing assembly may be configured to receive a projection or protrusion on the rotating drum of a gantry on a therapeutic radiotherapy device. The bearing assembly may be adjustable. The bearing assembly may form part of, or be connected to, a bracket or other connector or mounting means that is configured to engage or hold the monitor. The connector assembly may comprise the bearing assembly and such a bracket or other mounting means. The connector assembly may include a bias, such as a spring bias, to keep the monitor in place and/or to help resist movement of the monitor when the rotatable member rotates. A bias, such as a spring bias, may be included to enable the connector assembly to connect to different monitors of different respective sizes or thicknesses.

The first part of the connector assembly, which is configured for rotation with the first rotatable member, may be concentric with the second part of the connector assembly, which is configured for non-rotation with the monitor (and optionally with the counterweight). For example, the first and second parts may form part of a bearing assembly that comprises substantially concentric components. However, the first and second parts need not themselves be circular. For example, the first part and/or the second part of the connector assembly may comprise one or more arc shapes. The first part and the second part of the connector assembly may each comprise a single component or may each comprise more than one components.

The connector assembly may comprise a bracket configured to mechanically engage at least part of the monitor. The connector assembly may be connected to the counterweight. For example, the connector assembly may include a portion that is configured to hold, house or affix to the counterweight. The connector assembly may comprise an upper portion, configured to connect to the monitor, and a lower portion, configured to connect to the counterweight.

The counterweight may be connected or linked to the monitor, via the connector assembly or otherwise, so that the counterweight is located substantially vertically below the monitor, when the monitor is in an upright position. The counterweight may be configured to assist a bearing assembly, or other means, in preventing the monitor from rotating when surrounding components, such as components of a gantry of a therapeutic radiotherapy device, rotate. The counterweight may be configured to lower a gravitational centre of an assembly or entity that includes the monitor and the connector assembly. The counterweight may be configured to bias (or to help bias) the monitor to an upright position.

The connector assembly may be configured to locate the monitor at a rotational centre of the first rotatable member. The connector assembly may be configured to locate the monitor so that it is surrounded by one or more rotating parts of the first rotatable member, but is not necessarily at its rotational centre.

The connector assembly may comprise more than one bracket and/or more than one bearing assembly. The monitor may comprise one or more screens. There may be more than one counterweight.

The connector assembly may be provided integral to the monitor. For example, the connector assembly may extend from a rear face or rear portion of the monitor.

The rotation of the first part of the connector assembly, with the first rotatable member, may not change the position of the first part of the connector assembly (in one or more of the linear x, y, or z axes), relative to the monitor. For example, the first part of the connector assembly may comprise a component that rotates or rolls 'in situ' whilst maintaining a fixed linear position, relative to the monitor. For example, the first part of the connector assembly, which is configured to rotate with the first rotatable member, may comprise a ball bearing or other component that is configured to roll or rotate when the first rotatable member rotates, but which is not configured to also move axially. The first part of the connector assembly may be in direct connection with (a part of) the monitor. In such an arrangement, the second (non-rotating) part of the connector assembly may be integral to the monitor. Alternatively, the second part of the connector assembly may comprise a stationary (non-moving) connection means.

The first part of the connector assembly may be affixed to, or integral to, the first rotatable member on a therapeutic radiotherapy device. For example, the first rotatable member may comprise a gantry and the first part of the connector assembly may comprise part of the gantry. In such an arrangement, the second part of the connector assembly may be configured for non-rotation, with the monitor, but may comprise an intermediary component such as a ball bearing, that is configured to rotate or roll 'in situ', without changing position, relative to the monitor.

According to another aspect, a monitor connection assembly is provided for a radiotherapy device, said radiotherapy device being configured to provide therapeutic radiation to a patient via a source of therapeutic radiation, and wherein said radiotherapy device comprises a first rotatable member. The monitor connection assembly comprises a connector assembly configured to connect a monitor to the first rotatable member, and a counterweight. A first part of the connector is configured for rotation, with the first rotatable member, and a second part of the connector is configured for non-rotation, with the counterweight.

The monitor connection assembly may further comprise a monitor connected to the connector assembly.

According to another aspect a therapeutic radiotherapy device is provided comprising a monitor assembly for a radiotherapy device, said radiotherapy device being configured to provide therapeutic radiation to a patient via a source of therapeutic radiation, and wherein said radiotherapy device comprises a first rotatable member. The monitor assembly comprises a monitor configured for outputting visual data to a user, a counterweight, and a connector assembly configured to connect the monitor to the first rotatable member. A first part of the connector assembly is configured for rotation, with the first rotatable member, and a second part of the connector assembly is configured for non-rotation, with the monitor. The counterweight may be configured for non-rotation with the second part of the connector assembly. According to another aspect a therapeutic radiotherapy device is provided comprising a monitor connection assembly for a radiotherapy device, said radiotherapy device being configured to provide therapeutic radiation to a patient via a source of therapeutic radiation, and wherein said radiotherapy device comprises a first rotatable member. The monitor connection assembly comprises a connector assembly configured to connect a monitor to the first rotatable member, and a counterweight. A first part of the connector assembly is configured for rotation, with the first rotatable member, and a second part of the connector assembly is configured for non-rotation. The counterweight may be configured for non-rotation with the second part of the connector.

According to another aspect, a monitor assembly for a radiotherapy device is provided, said radiotherapy device being configured to provide therapeutic radiation to a patient via a source of therapeutic radiation, and wherein said radiotherapy device comprises a first rotatable member. The monitor assembly comprises a monitor configured for outputting visual data to a user, a counterweight, and a connector assembly configured to connect the monitor to the first rotatable member. A first part of the connector assembly is configured for movement, with the rotation of the first rotatable member, and a second part of the connector assembly is configured for non-movement, with the monitor.

Any suitable combination of the above aspects may be provided. Except where clearly mutually exclusive, a feature or parameter described in relation to any one of the above aspects or described herebelow in relation to a particular arrangement, may be applied to any other aspect or arrangement.

FIGURES

Specific arrangements are described herein, by way of example only, with reference to the figures, of which:

DETAILED DESCRIPTION

High-Level Overview of a LINAC Radiotherapy Device

Figure 1:
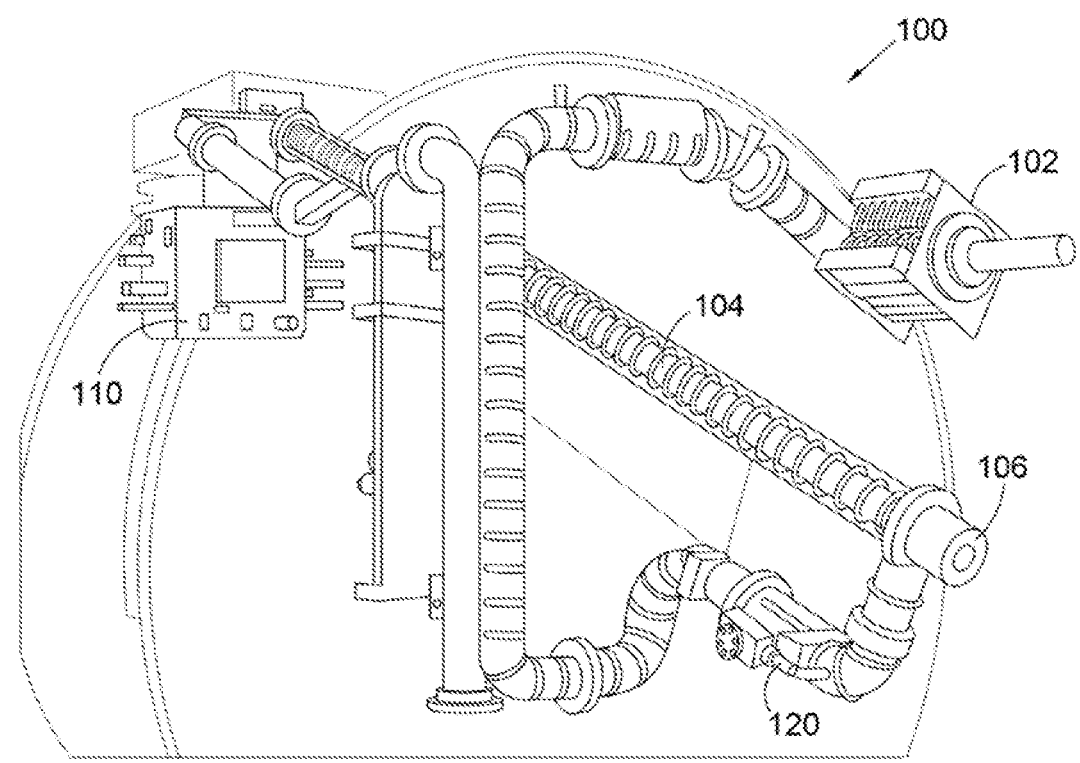
FIG. 1 shows an example Linear Accelerator (LINAC) device

FIG. 1 shows a known LINAC 100, suitable for delivering, and configured to deliver, a beam of radiation to a patient during radiotherapy treatment. In operation, the LINAC device 100 produces and shapes a beam of radiation and directs it toward a target region within the patient's body in accordance with a radiotherapy treatment plan.

A medical LINAC machine is by necessity complex, with many inter-operating component parts. A brief summary of the operation of a typical LINAC will be given with respect to the LINAC device 100 showed in FIG. 1 which comprises a source of radiofrequency waves 102, a waveguide 104, a source of electrons 106, a system capable of creating a strong vacuum comprising one or more vacuum pumps 120, a heavy metal target which produces X-rays when hit by an electron beam, and a complex arrangement of magnets capable of re-directing and focusing the electron beam onto the target. The device 100 depicted in FIG. 1 also comprises a treatment head which houses various apparatus configured to, for example, collimate and shape the resultant X-ray beam.

The source 102 of radiofrequency waves, such as a magnetron, produces radiofrequency waves. The source 102 of radiofrequency waves is coupled to the waveguide 104, and is configured to pulse radiofrequency waves into the waveguide 104. A source 106 of electrons, such as an electron gun, is coupled to the waveguide 104 and is configured to inject electrons into the waveguide 104. The injection of electrons into the waveguide 104 is synchronised with the pumping of the radiofrequency waves into the waveguide 104. The design and operation of the radiofrequency wave source 102, electron source 106 and the waveguide 104 is such that the radiofrequency (RF) waves accelerate the electrons to very high energies as they propagate through the waveguide 104.

As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they pass into a flight tube. The flight tube may be connected to the waveguide 104 by a connecting tube. This connecting tube or connecting structure may be called a drift tube.

The flight tube is kept under vacuum conditions by the pump system. The electrons travel along a slalom path toward the heavy metal target. The target may comprise, for example, tungsten. The slalom path allows the overall external length of the LINAC 100 to be reduced while ensuring that the beam of accelerated electrons, which is comprised of electrons with a small spread of energies, is focused on the target.

To ensure that propagation of the electrons is not impeded as the electron beam travels toward the target, the waveguide 104 is evacuated using a vacuum system comprising a vacuum pump 120 or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

When the high energy electrons hit the target, X-rays are produced in a variety of directions. The flight tube comprises a target window, which is transparent to X-rays, which is positioned to allow the X-rays to pass through the target window and into the treatment head 110. At this point, a primary collimator blocks X-rays travelling in certain directions and passes only forward travelling X-rays to produce a cone shaped beam. The X-rays are filtered, and then pass through one or more ion chambers for dose measuring. The beam can be shaped in various ways by beam-shaping apparatus, for example by using one or more block collimators and/or multi-leaf collimators, before it passes into the patient as part of therapeutic radiotherapy treatment.

In some implementations, the LINAC 100 is configured to emit either an X-ray beam or an electron particle beam. Such implementations allow the device to provide electron beam therapy, i.e. a type of external beam therapy where electrons, rather than X-rays, are directed toward the target region.

A typical LINAC device such as the device 100 shown in FIG. 1 also comprises several other components and systems. The whole system is cooled by a water cooling system (not shown in the figures). In order to ensure the LINAC does not leak radiation, appropriate shielding is also provided. As will be understood by the person skilled in the art, a LINAC device used for radiotherapy treatment will have additional apparatus such as a gantry to support and rotate the LINAC, a patient support surface, and a controller or processor configured to control the LINAC.

Rotatable Gantry

Figure 2:
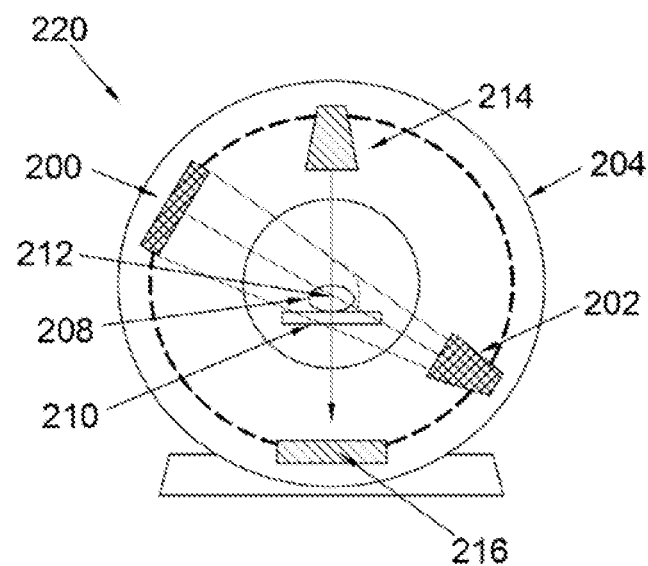
FIG. 2 shows an example LINAC device with a rotating gantry which houses a radiation source and a radiation detector

FIG. 2 shows a cross section through a co-planar LINAC radiotherapy device 220 configured to provide co-planar radiotherapy treatment. A patient 208 is shown located on a table or other support surface 210, within the central part of the device 220.

The device 220 comprises a rotatable housing or gantry 204. The gantry 204 is generally rotatable about the centrepoint of the depicted cross-section—i.e. the gantry's 204 axis of rotation is generally perpendicular to the plane of the depicted cross-section. The gantry 204 has a radiation source (or 'radiation head') 200 mounted thereon and a radiation detector 202. In the arrangement shown, the radiation detector 202 is mounted substantially diametrically opposite the radiation head 200, on a circular support track of the gantry 204. Therefore rotation of the gantry 204 causes rotation of the radiation head 200 and of the detector 202, in this arrangement. Moreover, the detector 202 and the radiation head 200 are arranged to rotate together, such that they are always arranged substantially 180 degrees from one another (i.e. diametrically opposite one another) around the gantry 204.

The radiation head 200 is arranged to emit a targeted X-ray beam, directed towards a tumour or other target area within the patient's body. The radiation detector 202 is arranged to detect the beam, once it has passed through the patient's body. The directionality of the beam is controlled, at least in part, by one or more collimators, which are discussed below.

In operation of the LINAC 220, radiation is emitted in the plane of the depicted cross section, i.e. perpendicular to the axis of rotation of the radiation source 200, radiation detector 202 and gantry 204. Radiation can thus be delivered to a radiation isocentre 212 at the centrepoint of the gantry 204, regardless of the angle to which the radiation head 200 is rotated. This therefore enables the radiation head 200 to direct radiation towards a tumour or other target area within the patient 108, from various different angles around the patient 108. As discussed above, this is an important feature of any therapeutic radiotherapy device, to ensure that the radiation does not have to repeatedly pass through the same portion of healthy tissue within the patient, in order to reach the target area. Instead, the radiation head 200 can be rotated to different rotational angles, so that the radiation beam passes through multiple different healthy areas, each for a limited time period, during the therapeutic radiotherapy treatment of the tumour or other target area.

This arrangement also comprises an imaging radiation source 214 and an imaging radiation detector 216. The imaging radiation source 214 and the imaging radiation detector 216 are arranged substantially diametrically opposite one another, on the gantry 204, and rotate together, with the gantry 204, such that they remain substantially diametrically opposite one another, throughout operation of the Linac device 220.

Collimation of the Beam

In order to target a tumour or other target area and reduce the exposure of healthy tissue to radiation, it is important to locate the patient correctly within a therapeutic radiotherapy device, so that the target area is at the radiation isocentre 212. Thus, the table or other support surface 208 on which the patient is located is usually moveable both vertically and horizontally. Moreover, in order to successfully target the tumour or other target area, the shape of the radiation beam should be arrangeable to fit the shape, size and nature of the tumour, as closely as possible.

Most tumours can be targeted using a combination of block collimators and a so-called "multi-leaf" collimators (MLC's). A block collimator is usually a solid block of radiopaque material such as tungsten, which usually has a straight front edge that spans the entire width of an aperture, from which the radiation beam is emitted, and which can be advanced and/or withdrawn across the aperture in a direction transverse to the front edge. Thus, the block collimator has the effect of adjusting the width of the aperture as needed. A pair of such collimators arranged face-to-face can thus narrow the aperture from both opposing sides. A multi-leaf collimator (MLC) comprises an array of long, narrow, deep leaves' of radiopaque material that, in some arrangements, can each be extended into and out of the aperture. Arranged side-by-side in an array; the tips of the leaves therefore define a chosen shape which can be varied at will by extending or retracting individual leaves.

According to an arrangement described herein, the collimator (or collimators) is/are provided on or within the radiation head 200 which is attached to the rotatable gantry 204 of the LINAC device 220. The radiation beam from the radiation head 200 is directed towards the isocentre of gantry rotation and the collimator delimits the beam to a desired beam shape. The collimator may include a block collimator and/or an MLC.

Monitoring and Controlling Operation of a Therapeutic Radiotherapy Device

An improved rotatable gantry will now be described, in relation to FIGS. 3(*a*) to 6, herein.

Figure 3A:
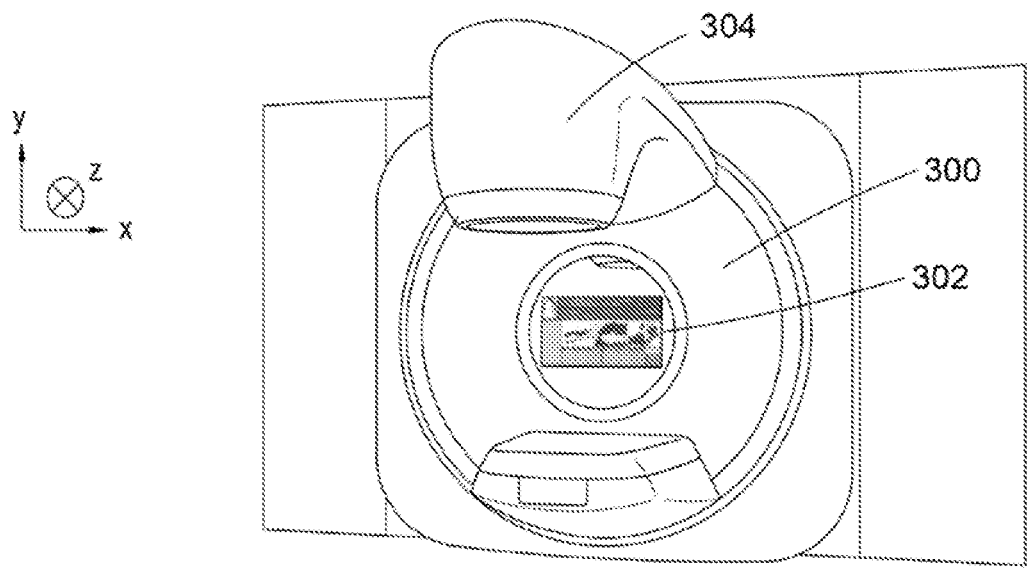
FIG. 3(a) shows an improved rotatable gantry of a Linac device
Figure 3B:
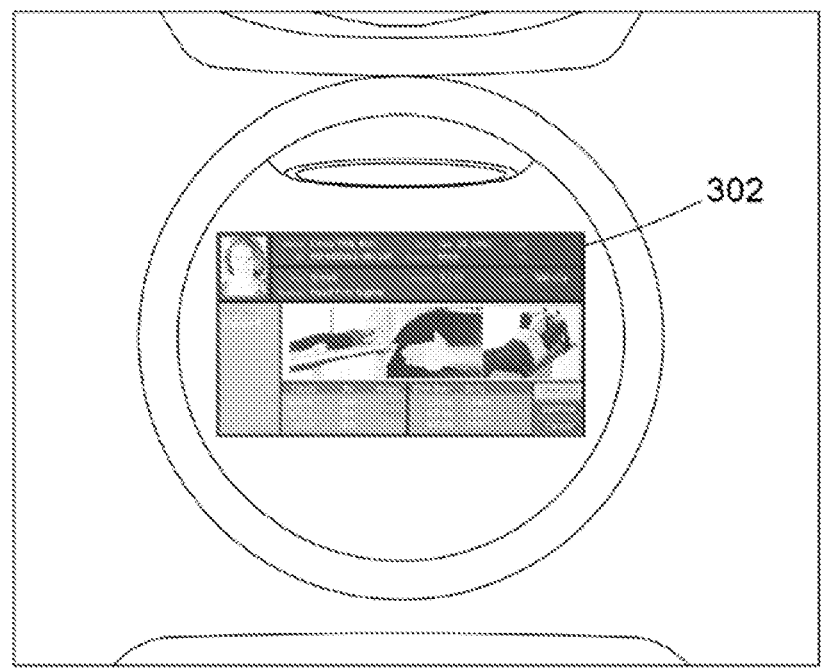
FIG. 3(b) shows a closer view of the monitor in the improved rotatable gantry of FIG. 3(a)

An arrangement of an improved rotatable gantry 300 of a Linac device is shown in FIG. 3(*a*). The rotatable gantry 300 has a monitor 302 provided substantially at its centre, as discussed further below. The rotatable gantry 300 also comprises a radiation head 304. The rotatable gantry 300 is arranged to rotate about a substantially central rotational axis (the z axis in FIG. 3(*a*)), to enable the radiation head 304 to deliver radiation from multiple different angles, relative to a patient. The patient would be located on a patient table (not shown) which is moveable and locatable so that the radiation from the radiation head 304 hits a target area on the patient, such as a tumour, from the multiple different angles, as selected by the user (i.e. the operator), during operation of the Linac device.

The monitor 302 can be seen more closely in FIG. 3(*b*). As shown therein, in this arrangement, the monitor 302 displays patient identifying information, data regarding the patient's tumour(s), multiple visual images of the patient and some operating data.

During operation of the Linac device, the user (i.e. the operator) of the device can look at the monitor 302, and use the information displayed thereon to guide his or her control of the device. The location of the monitor 302, substantially at the centre of the rotatable gantry 300 is convenient and helpful for the user. When the user operates the treatment table and relevant accessories, to setup the patient for treatment, the location of monitor 302 at the centre of the rotatable gantry 300 enables him or her to inspect the monitor display without having to move away from his or her current position, at or near to the Linac device. The user can therefore view the content that is displayed by the monitor 302 more intuitively and clearly, which enables him or her to quickly and accurately setup the patient. The location of the monitor 302 at the centre of the rotatable gantry 300 is generally at a good height, for the user's eye level. It also is a compact solution as it avoids the need to provide a monitor elsewhere in the treatment room.

In known Linac devices, it has been problematic to provide a monitor within a rotatable gantry, because the monitor would rotate with the surrounding parts of the gantry. Therefore, at certain times during rotation, the monitor would be upside down or sideways or at another awkward angle, making it hard for the user to use the monitor reliably. In the improved gantry 300 described herein, the monitor 302 is configured to remain substantially stationary—and the visual information thereon to therefore remain upright, from the user/operator's visual perspective, throughout use of the Linac device. The monitor 302 can remain upright, regardless of whether, when, how often and by how much the surrounding parts of the gantry 300, and/or any other parts of the device such as a collimator, the patient table and so on, move or rotate.

Figure 4:
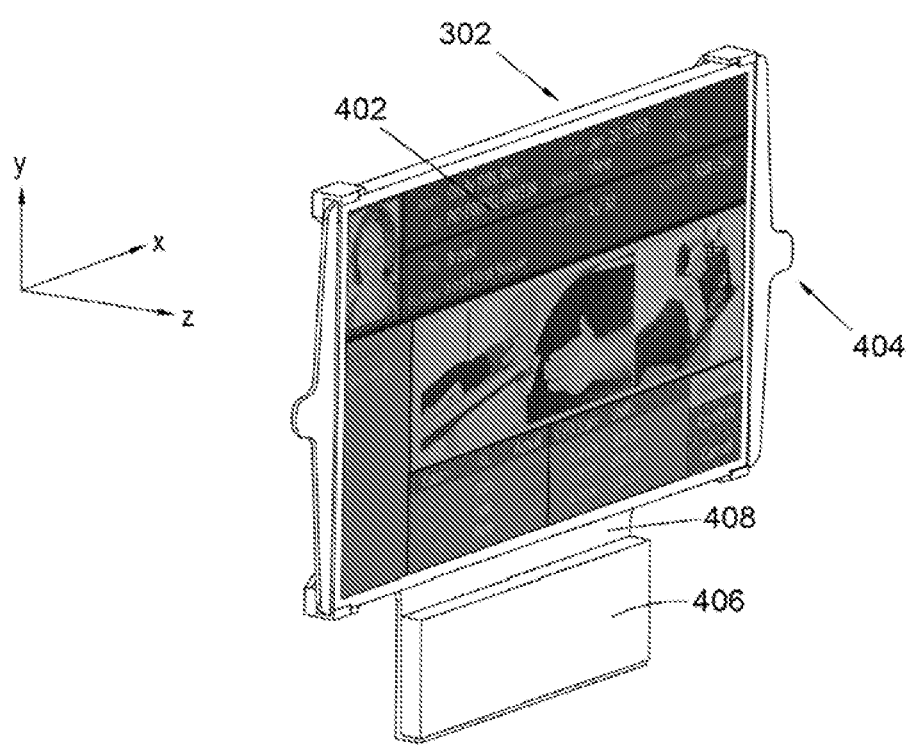
FIG. 4 shows an improved monitor and bracket assembly

FIG. 4 shows an assembly including the monitor 302 of the improved rotatable gantry 300, not in situ within the gantry 300. A front face of the monitor 302 comprises a substantially rectangular screen 402, on which visual information can be displayed. It also comprises a power supply for operating the monitor 302 and suitable monitor electronics for relaying information to it, to be displayed on the screen 402, however these are not shown nor discussed in further detail herein. There is a bracket 404 provided, which extends across the rear face of the monitor 302 and grips the monitor 302 at its four corners. The bracket 404 is configured for mounting the monitor 302 to the gantry 300, as discussed further below. There is also a counterweight 406, which is provided substantially vertically below the monitor 302, when the monitor 302 is in an upright position, and which is configured to change the mass characteristics of the monitor/bracket assembly. The counterweight 406 helps to keep the monitor 302 stationary whilst the gantry 300 rotates around it.

In this arrangement, the bracket 404 includes a downwardly projecting portion 408 which is laterally narrower than the screen 402 (and therefore laterally narrower than the main body of the bracket 404, which extends across the full width of the rear face of the monitor 302) and which projects substantially downwards, away from the screen 402, when the monitor 302 is in an upright position. The downwardly projecting portion 408 is, in this arrangement, L-shaped in cross section. That is; the downwardly projecting portion 408 is substantially planar for the most part, with a short shelf 410 extending outwards (in the z direction) at approximately 90° to its planar part. In this arrangement, the counterweight 406 is substantially cuboidal, and is sized so as to sit within the 'L-shape' of the downwardly projecting portion 408. It will be appreciated that, in other arrangements, the precise size and shapes of the bracket and counterweight could be different to those shown and describe din detail herein, whilst still providing the same mechanical effects.

In this arrangement, The bracket is made of an aluminium alloy and the counterweight is made of copper or steel. Other suitable materials may be used, in other arrangements, As can be better seen from FIG. 5(*a*) herein, the bracket 404 in this particular arrangement includes a substantially 'X' shaped support 504, extending from the top left hand corner to bottom right hand corner and from the top right hand corner to bottom left hand corner of the rear face of the monitor 302. It also comprises longitudinal tabs 506*a*, 506*b* which extend substantially down the sides of the monitor 302, from top left hand corner to bottom left hand corner and from top right hand corner to bottom right hand corner. It also includes lateral tabs 508*a*, 508*b* which extend substantially to the left and to the right, from the centre of the 'X' shaped support 504, across part of the width of the rear face of the monitor 302. The lateral tabs 508*a*, 508*b* include springs 509*a*, 509*b* that act to push the monitor 302 towards the front inner wall of bracket 404, so that monitor 302 can be placed in the bracket stably, ensuring that the monitor 302 does not move or shake inside the bracket 404 when the gantry 300 is rotating. It will be appreciated that, in other arrangements, alternative means might be provided for ensuring that the monitor remains secure and stable, whilst the gantry is rotating.

In this arrangement, the branches of the substantially 'X' shaped support 504 do not meet at a single point at its centre. Instead, there is a bearing assembly 510 provided at the centre of the substantially 'X' shaped support 504. The bearing assembly 510 is configured to hold the monitor 302 in place substantially at the rotational (or axial) centre of the gantry 300, and to enable it to remain substantially stationary whilst the rotating part (also known as 'the drum') of the gantry 300 rotates around it.

Figure 5A:
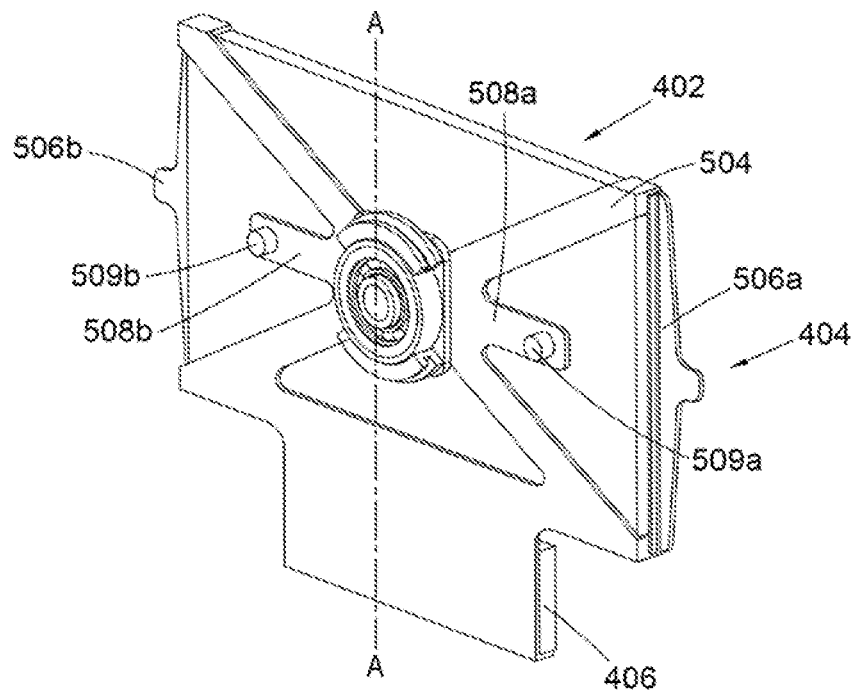
FIG. 5(a) shows a rear view of the improved monitor and bracket assembly of FIG. 4
Figure 5B:
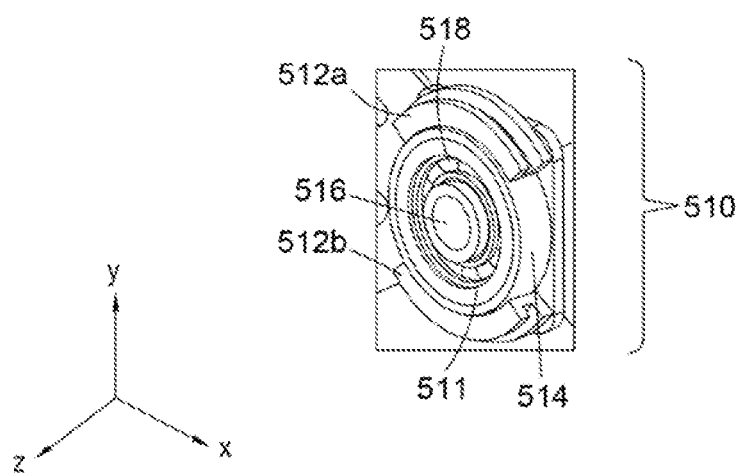
FIG. 5(b) shows an expanded view of a bearing assembly within FIG. 5(a)
Figure 6:
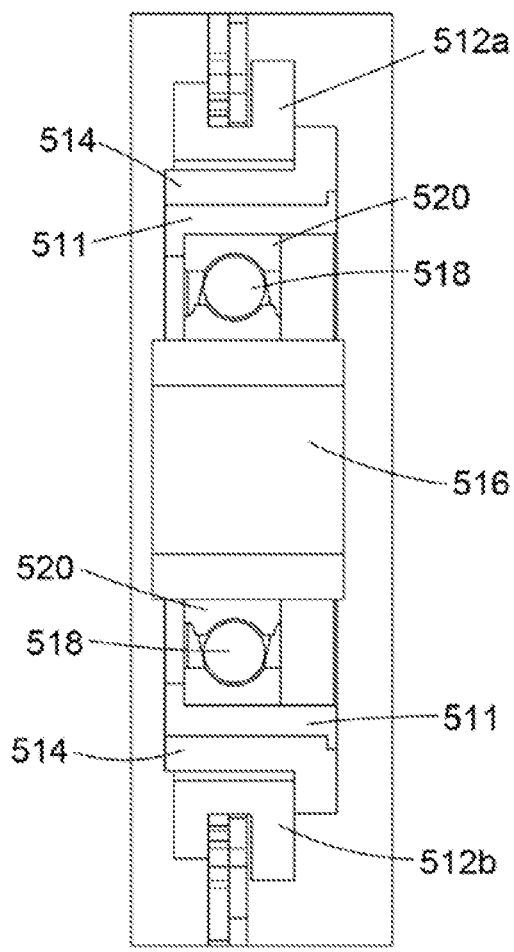
FIG. 6 shows a cross-sectional view along the line A-A in FIG. 5(a)

As shown in FIGS. 5(*b*) and 6, the bearing assembly 510 comprises a hollow shaft 516 at its axial centre, which does not move with the rotating gantry 300. The hollow shaft 516 is affixed to the bracket 404, which extends across and grips the rear face of the monitor 302. Therefore the bracket 404 and monitor 302 will not move, but will stay stationary with the hollow shaft 516, when the rotating gantry 300 rotates. For example, the hollow shaft may be screw-fixed to the bracket 404. In some arrangements, the shaft may not be hollow.

The hollow shaft 516 is surrounded by bearings 518 housed in a bearing holder 520. The bearings 518 and bearing holder 520 are provided radially between the shaft 516 and an adjustable base 514, which is discussed further below. The operation of bearings of this type will be familiar to the skilled reader. In short; the bearings enable the radially outer parts of the bearing assembly 510 to rotate freely with the rotating gantry 300, whilst enabling the radially inner part of the bearing assembly 510—i.e. the hollow shaft 516—to remain stationary, in a manner that creates very little friction or other resistance between the moving and stationary components.

The bearing assembly also includes first 512*a* and second 512*b* substantially arc-shaped grooves, provided substantially at the top and the bottom of the bearing assembly 510, respectively. These arc-shaped grooves 512*a*, 512*b* extend over part of the top, and under part of the bottom, respectively, of circular components of the bearing assembly, which are provided radially inward of the arc-shaped grooves 512*a*, 512*b* and which are described in more detail below. The arc shaped grooves 512*a*, 512*b* are substantially 'U-shaped' in cross-section, and are configured to receive projections or other formations that are part of the rotating drum of the gantry 300. The arc-shaped grooves 512*a*, 512*b* therefore act to hold the bearing assembly 510 fixed in the drum centre of the gantry 300, and are configured to rotate with the gantry 300.

The bearing assembly 510 further comprises, in this arrangement, an adjustable base 514. The adjustable base 514 comprises a substantially cylindrical portion, provided radially just inward of the arc-shaped grooves 512*a*, 512*b*, and a lip or flange which extends at substantially 90° away from the base of the cylindrical portion, in the x-y plane. The adjustable base 514 is configured to adjust the concentricity of the gantry 300 and the bearing assembly 510. For example, the adjustable base 514 is, in this arrangement, screwed to the arc-shaped grooves 512*a*, 512*b*. The screw through-holes (not shown) for fixing the adjustable base 514 to the arc-shaped grooves 512*a*, 512*b* has a certain gap, which allows the adjustable base 514 to adjust its fixed position within the gap. An adjustment can be made, during set up, to align the centre of the hollow shaft 516, which is the centre of rotation of the bearing assembly 510, with the rotational centre of the gantry 300. For example, the user may align the centre of the hollow shaft 516 with the rotational centre of the gantry 300 using a laser, that can be provided within or in conjunction with the Linac device, There is, in this arrangement, a bushing 511 located between the bearing holder 520 and the adjustable base 514. The bushing 511 may be omitted in some arrangements. It is, in this arrangement, assembled with the bearing 518, 520 and can be pushed in and out from the adjustable base 514 without the entire bearing assembly 510 having to be removed away from the gantry drum. The purpose is to facilitate maintenance for cable routing work inside the gantry 300, and to enable the bracket to be quickly disassembled in order to reveal the inside of the gantry 300, for access for example for maintenance. It will be appreciated that an alternative means may be provided in some arrangements, to provide user access inside the gantry without requiring complete disassembling of the monitor support means.

As mentioned above, the counterweight 406 helps the monitor 302 and the bracket 404 (and the shaft 516) to remain stationary whilst the gantry 300 and the radially outward parts of the bearing assembly 510 rotate therearound. It does so by providing a relatively heavy weight below the monitor 302, affixed to (or otherwise held by) a lower part of the bracket 404, thereby substantially lowering the centre of gravity of the monitor/bracket assembly. This lower centre of gravity helps the monitor/bracket assembly to resist being rotated by the surrounding rotating parts of the gantry 300. In effect, even if the monitor/bracket assembly started to rotate slightly with the surrounding rotating parts of the gantry 300, the weight of, and the downward gravitational pull on, the counterweight 406 would bias the monitor/bracket assembly to return to its 'neutral' position, in which the monitor 302 is substantially upright and the counterweight 406 is located vertically below the monitor 302.

By providing this improved monitor within a Linac device (or other therapeutic radiotherapy device), the arrangements described herein enable the monitor to remain upright, and thus for the contents that it displays to be readily visible by the user throughout operation of the device. At the same time, the arrangements enable the monitor to be provided within the centre of the rotating gantry, which is space-efficient and practical for the user, as he or she often needs to look at the rotating gantry during operation of the Linac device for application of therapeutic radiation.

The bracket, counterweight and bearing described herein, which enable the monitor to remain upright, whilst the gantry rotates therearound, are physically relatively simple and inexpensive to manufacture. They are also relatively lightweight and compact. Therefore the inclusion of a bracket, counterweight and bearing—or of a similar assembly that enables the monitor to remain fixed whilst the gantry rotates therearound—does not add significantly to manufacture time or costs, for a therapeutic radiotherapy device.

The improved gantry and monitor described herein can enable the user to monitor operation of the device, and the behaviour and wellbeing of the patient, more readily and more accurately. This will provide improved user satisfaction and will increase the accuracy of the user's control of the device. Therefore, the effectiveness of the radiotherapy that he or she can provide, for treating the patient's target region, will improve. This also has the effect of reducing delays, which could otherwise occur with devices in which an inferior or less user-friendly monitor was provided, thus improving patient throughput and improving overall experience for individual patients. This could also lead to cost savings, if the device is being used more efficiently. The improved gantry and monitor described herein can also increase the speed and facility with which a new or infrequent user of the device can monitor operation (and his or her control) of a therapeutic radiotherapy device; which limits the risk of user error or inaccuracy and also increases the usefulness of the therapeutic radiotherapy device to the hospital or other facility where it is used, because it makes the device readily useable by a greater number of users.

Variations

It will be appreciated that a particular arrangement has been described in detail herein but that variations may be provided. For example, the precise configuration of the bracket, and the manner in which it grips or is otherwise affixed to the monitor, may be varied. The monitor may be connected to the gantry by a connector other than a bracket. Any suitable connector or connector assembly may be employed between the monitor and the gantry, wherein a part of the connector or connector assembly is configured to move (for example to rotate) with the gantry's rotation and a part of it is configured to keep the monitor upright.

According to some arrangements, a first part of a connector assembly, which connects the monitor to the gantry, is configured to move when the gantry rotates, and a second, different part of that connector assembly is configured for non-movement when the gantry rotates. The part of the connector or connector assembly that is configured to move, with the rotation of the gantry, may move rotationally or linearly, or it may exhibit a combination of rotational and linear movement. The part of the connector or connector assembly that is configured to move may not change its linear (or axial) position relative to, or extent of separation from, the monitor. For example, the part of the connector or connector assembly that is configured to move may comprise a component such as a ball bearing that is configured to rotate or roll 'on the spot', in a fixed position with respect to the monitor. Alternatively, the movement may cause that part of the connector to move towards or away from (at least a part of) the monitor. According to a variation on such an arrangement, the second part of the connector assembly may exhibit some movement when the gantry rotates but will ensure that the monitor does not rotate, with the gantry. For example, the second part of the connector assembly may not rotate but may move in a linear (or axial) manner.

The part of the connector or connector assembly that is configured to move may be integral to a rotating part of a therapeutic radiotherapy device, such as a gantry.

The connector may, for example, not include an X shaped portion, and/or longitudinal tabs and/or lateral tabs as described herein. Instead it may comprise any other suitable formation(s) configured to support a monitor, and to house or attach to a counterweight. Similarly, the precise size, shape, thickness of the monitor, counterweight and bearing assembly components may vary. The counterweight may be integral to the connector, or it may be a separate component that is attached to or housed by the connector.

The counterweight may not, in some arrangements, remain in a fixed position. In some arrangements, the counterweight may be arranged to move in order to counteract movement of the gantry (and of a part or parts of a connector between the monitor and the gantry) in order to maintain the monitor in a substantially stable, upright position.

The monitor may not be provided at the rotational centre of the gantry but may simply be provided radially inward of the rotating part(s) of the gantry.

Any directional or positional terms used herein such as 'left', 'right', above', 'below', 'upper', 'lower' 'inward', 'outward'. 'longitudinal', lateral' and so on, are used in relative terms and are not intended to be limiting.

Any section headings used herein are merely for organisational purposes. They are not to be construed as limiting or dividing the subject matter disclosed in the application as a whole.

It is to be understood that the above description is intended to be illustrative, and not restrictive. Many other implementations will be apparent to those of skill in the art upon reading and understanding the above description. Although the present disclosure has been described with reference to specific example implementations, it will be recognised that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the HI scope of equivalents to which such claims are entitled.

The invention claimed is:

1. A monitor assembly for a radiotherapy device, said radiotherapy device being configured to provide therapeutic radiation to a patient via a source of therapeutic radiation, and wherein said radiotherapy device comprises a first rotatable member configured to rotate around a central axis, wherein the monitor assembly comprises:
   a monitor configured for outputting visual data to a user;
   a counterweight; and
   a connector assembly configured to connect the monitor to the first rotatable member, wherein a first part of the connector assembly is configured for rotation with the first rotatable member around the central axis, and wherein a second part of the connector assembly is configured for non-rotation with the monitor and configured to hold the monitor in place at a rotational center of the first rotatable member.

2. The monitor assembly of claim 1, wherein said first rotatable member includes a rotatable gantry.

3. The monitor assembly of claim 1, wherein the source of therapeutic radiation is provided on or within the first rotatable member.

4. The monitor assembly of claim 1, wherein the connector assembly includes a bearing assembly.

5. The monitor assembly of claim 1, wherein the connector assembly includes a bracket configured to mechanically engage at least part of the monitor.

6. The monitor assembly of claim 1, wherein the connector assembly is connected to the counterweight.

7. The monitor assembly of claim 6, wherein the connector assembly includes:
   an upper portion, configured to connect to the monitor; and
   a lower portion, configured to connect to the counterweight.

8. The monitor assembly of claim 1, wherein the first part of the connector assembly is concentric with the second part of the connector assembly.

9. The monitor assembly of claim 1, wherein the connector assembly is configured to locate the monitor at the rotational center of the first rotatable member.

10. A monitor connection assembly for a radiotherapy device, said radiotherapy device being configured to provide therapeutic radiation to a patient via a source of therapeutic radiation, wherein said radiotherapy device comprises a first rotatable member configured to rotate around a central axis, and wherein the monitor connection assembly comprises:

a connector assembly configured to connect a monitor to the first rotatable member; and a counterweight, wherein a first part of the connector assembly is configured for rotation with the first rotatable member around the central axis, and wherein a second part of the connector assembly is configured for non-rotation and configured to hold the monitor in place at a rotational center of the first rotatable member.

11. The monitor connection assembly of claim 10, further comprising:

a monitor connected to the connector assembly.

12. A therapeutic radiotherapy device comprising:

a first rotatable member configured to rotate around a central axis; and a monitor assembly, the monitor assembly including:
   a monitor to output visual data to a user;
   a first counterweight; and
   a monitor connection assembly, the monitor connection assembly including:
      a connector assembly configured to connect the monitor to the first rotatable member wherein a first part of the connector assembly is configured for rotation with the first rotatable member around the central axis, and wherein a second part of the connector assembly is configured for non-rotation and configured to hold the monitor in place at a rotational center of the first rotatable member; and
   a second counterweight.

13. The therapeutic radiotherapy device of claim 12, wherein the therapeutic radiotherapy device is configurable to provide therapeutic radiation to a patient via a source of therapeutic radiation, and wherein the source of radiation is provided on or within the first rotatable member.

14. The therapeutic radiotherapy device of claim 13, wherein the second part includes a stationary connection member for connecting the second part to the monitor.

15. The therapeutic radiotherapy device of claim 13 wherein the second part includes an intermediary component configurable to rotate or roll 'in situ', without changing position relative to the monitor.

16. The therapeutic radiotherapy device of claim 13, wherein the first counterweight is configurable for non-rotational movement with the monitor, and wherein the second counterweight is configurable for non-rotational movement with the second part of the connector assembly.

17. The therapeutic radiotherapy device of claim 13, wherein the first part of the connector assembly is concentric with the second part of the connector assembly, and wherein the connector assembly is configurable to locate the monitor at a rotational center of the first rotatable member.

* * * * *